(12) United States Patent
Kim et al.

(10) Patent No.: US 6,410,004 B1
(45) Date of Patent: Jun. 25, 2002

(54) POLYUREAS AND WATER-SOLUBLE OR WATER-DISPERSIBLE POLYMERIC SALTS

(75) Inventors: Son Nguyen Kim, Hernsbach; Axel Sanner, Frankenthal; Peter Hössel, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/523,695

(22) Filed: Mar. 13, 2000

(30) Foreign Application Priority Data

Mar. 12, 1999 (DE) ......................... 199 10 996

(51) Int. Cl.⁷ .................................. A61K 7/06
(52) U.S. Cl. .................. 424/70.1; 528/44; 528/68; 528/71; 528/72; 528/85; 528/83; 528/38; 525/50; 525/452; 525/457; 524/507; 424/70.12; 424/70.16; 424/70.17
(58) Field of Search ............... 528/44, 68, 71, 528/72, 85, 83, 38; 525/50, 452, 457; 524/507, 70.1, 70.12, 70.16, 70.17

(56) References Cited

U.S. PATENT DOCUMENTS

| | | | |
|---|---|---|---|
| 3,223,751 A | 12/1965 | Sellet | 260/885 |
| 3,565,973 A | 2/1971 | Michaels | 260/874 |
| 3,836,537 A | 9/1974 | Boerwinkle et al. | 260/29.6 |
| 4,192,861 A | 3/1980 | Micchelli | 424/47 |
| 4,237,253 A | 12/1980 | Jacques et al. | 526/75 |
| 4,299,817 A | * 11/1981 | Hannan, III et al. | |
| 4,501,834 A | * 2/1985 | Su | |
| 4,761,273 A | 8/1988 | Grollier et al. | 424/47 |
| 4,814,101 A | 3/1989 | Schieferstein et al. | 252/174 |
| 5,306,484 A | 4/1994 | Potthoff-Karl et al. | 424/47 |
| 5,958,390 A | 9/1999 | Sanner et al. | 424/70.1 |

FOREIGN PATENT DOCUMENTS

| | | |
|---|---|---|
| CA | 2066226 | 3/1991 |
| CA | 2148805 | 6/1994 |
| DE | 28 17 369 | 10/1978 |
| DE | 29 17 504 C3 | 11/1979 |
| DE | 37 08 451 A1 | 10/1988 |
| DE | 39 01 325 A1 | 7/1990 |
| DE | 39 29 973 A1 | 3/1991 |
| DE | 42 14 305 C2 | 11/1992 |
| DE | 42 25 045 A1 | 2/1994 |
| DE | 42 41 118 A1 | 6/1994 |
| DE | 43 14 305 A1 | 11/1994 |
| DE | 195 41 326 A1 | 5/1997 |
| DE | 195 41 329 A1 | 5/1997 |
| DE | 195 41 658 A1 | 5/1997 |
| DE | 197 09 277 A1 | 9/1998 |
| EP | 0 636 361 A1 | 2/1965 |
| EP | 0 619 111 B1 | 10/1994 |
| EP | 0 859 804 | 8/1998 |
| GB | 1 321 836 | 7/1973 |
| JP | A-7127480 | 4/1968 |
| JP | A-3206 023 | 12/1989 |
| JP | A3206 024 | 12/1989 |
| WO | WO 89/12438 | 12/1989 |
| WO | WO 94/03515 | 2/1994 |
| WO | WO 97/17052 | 5/1997 |
| WO | WO 97/17386 | 5/1997 |
| WO | WO 97/25021 | 7/1997 |

OTHER PUBLICATIONS

E. Fikentscher, Cellulose–Chemie 13 (1932), pp. 58–64.

* cited by examiner

*Primary Examiner*—Robert Dawson
*Assistant Examiner*—Kuo-Liang Pang
(74) *Attorney, Agent, or Firm*—Keil & Weinkauf

(57) ABSTRACT

The present invention relates to polymers, polyureas and water-soluble or water-dispersible polymeric salts, a cosmetic or pharmaceutical composition which comprises at least one such polymer, and to the use of the polymers.

13 Claims, No Drawings

POLYUREAS AND WATER-SOLUBLE OR WATER-DISPERSIBLE POLYMERIC SALTS

The present invention relates to polyureas and water-soluble or water-dispersible polymeric salts, to the use of these polymers, and to compositions which comprise these polymers.

In cosmetics, polymers with film-forming properties are used for setting, shaping and improving the structure of hair. These hair-treatment compositions generally comprise a solution of the film former in an alcohol or a mixture of alcohol and water.

Hair-treatment compositions, in particular hair-setting compositions, are generally sprayed onto the hair in the form of aqueous-alcoholic solutions. After the solvent has evaporated, the hair is held in the desired shape at the mutual points of contact by the polymer which remains. The polymers should on the one hand be sufficiently hydrophilic that they can be washed out of the hair, but on the other hand they should be hydrophobic so that the hair treated with the polymers retains its shape even at high atmospheric humidity, and does not stick together. In order to obtain as highly an efficient hair-setting action as possible, it is also desirable to use polymers which have a relatively high molecular weight and a relatively high glass transition temperature (at least 10° C.).

A further current demand on hair-treatment compositions is that they should give the hair flexibility, a natural appearance and shine, even, for example, when the hair is by its very nature particularly strong and/or dark.

A further consideration when formulating hair-setting compositions is that, because of the environmental regulations governing the emission of volatile organic compounds (VOC) into the atmosphere, it is necessary to reduce the content of alcohol and propellant.

It is known to use water-soluble or dispersible polyurethanes in cosmetics. Thus, because, for example, they have film-forming properties and, in general, a low viscosity in water/ethanol, they are suitable for use in hair cosmetics, such as, for example, for formulating low-solvent hair sprays.

DE-A-42 25 045 and WO 94/03515 describe the use of water-soluble or water-dispersible anionic polyurethanes as hair-setting agents.

The acid groups present in these polyurethanes can be converted into the corresponding salts by neutralization with at least one base. For this purpose, low molecular weight amines, such as 2-amino-2-methylpropanol, diethylaminopropylamine and triisopropanolamine, are used.

EP-A-619 111 describes the use of polyurethanes based on organic diisocyanates, diols and 2,2-hydroxymethyl-substituted carboxylates in hair fixative compositions. Here, at least some of the carboxyl groups are neutralized with an organic or inorganic low molecular weight base.

DE-A-195 41 658 describes water-soluble or water-dispersible graft polymers of a polyurethane prepolymer having terminal isocyanate groups and a protein containing free amino groups.

EP-A-636 361 describes a cosmetic composition comprising, in a cosmetically compatible carrier, at least one pseudolatex based on a polycondensate which comprises at least one polysiloxane unit and at least one polyurethane and/or polyurea unit having anionic or cationic groups. The neutralizing agents used here are mineral bases, low molecular weight amines and aminoalcohols, mineral acids and low molecular weight carboxylic acids. WO 97/25021 has a similar disclosure content. The wash-off of these film formers is unsatisfactory. In addition, because they have a high siloxane content they do not have the setting action required of a hair polymer.

DE-A-195 41 329 and WO 97/17052 describe hair-treatment compositions comprising a hair-setting polymer which is soluble or dispersible in water or in a water/alcohol mixture, and additionally a water-soluble or -dispersible siloxane-containing salt. Hairspray formulations based on these siloxane-containing salts, a non-siloxane-containing hair-setting polymer and a silicone oil lead to very smooth films.

DE-A-195 41 326 and WO 97/17386 describe water-soluble or water-dispersible polyurethanes having terminal acid groups, their preparation and their use. Here, a water-soluble or -dispersible polyurethane prepolymer having terminal isocyanate groups is reacted with an aminosulfonic acid or aminocarboxylic acid, in particular taurine, aspartic acid and glutamic acid.

DE-A-197 09 277 relates to polysiloxane-containing hair-setting compositions comprising from 0.5 to 15% by weight of carboxyl-containing polymers which, in neutralized form, are water-soluble or water-dispersible. The neutralizing agents used here are alkali metal carbonates, ammonia and amines and amino alcohols having at most 3 carbon atoms in the longest carbon chain.

None of the abovementioned documents describes polymeric salts of a polymeric cation and a polymeric anion, where polyurea or polyurethane is the polymeric anion and/or the polymeric cation. The polyurethanes described above lead to films which are in need of improvement with regard to their flexibility and thus with regard to the suppleness imparted to the hair.

It is known to use copolymers based on $\alpha,\beta$-ethylenically unsaturated mono- and/or dicarboxylic acids in haircare compositions.

GB-A-1 321 836 describes hair-setting compositions based on copolymers which comprise an unsaturated dicarboxylic acid and a vinyl or vinyldiene monomer in copolymerized form. From 5 to 20% of the carboxyl groups have been neutralized with primary $C_4$- to $C_{16}$-amines.

DE-A-29 17 504 describes an aerosol hairspray based on a copolymer of at least one unsaturated monocarboxylic acid and at least one vinyl or vinylidene monomer. Here, at least 7 to 100% of the carboxyl groups have been neutralized, at least half of which with a long-chain primary, secondary and/or tertiary amine having from 8 to 20 carbon atoms in the longest chain.

WO 89/12438 describes a hair-setting composition based on a hair polymer containing carboxyl groups which have been neutralized to at least 40 mol % with a long-chain amine chosen from amidoamines, N-ethoxylated amines and ether amines.

The abovementioned polyacrylates having carboxyl groups which have been neutralized with fatty amines or ethoxylated fatty amines lead to soft, tacky films with a drastically reduced setting action. These polymers are therefore of only very limited suitability for use as hair-setting agents.

JP-A-7127480 describes a hair-treatment composition based on an amine salt solution of a copolymer which comprises an unsaturated carboxylic acid in copolymerized form.

JP-A-03206023 describes a polymer resin for hair-treatment compositions which comprises, in copolymerized form, a) 6 to 35% by weight of acrylic acid, methacrylic acid, itaconic acid or a mixture thereof, b) 15 to 50% by weight of at least one $C_{10}$- to $C_{18}$-alkyl (meth)acrylate, c) 15 to 50% by weight of at least one $C_4$- to $C_8$-alkyl (meth) acrylate and d) 0 to 25% by weight of at least one other hydrophobic vinyl monomer. The resulting copolymers are neutralized with a base chosen from ammonia, morpholine, isopropanolamine and aminoethylpropanediol.

JP-A-03206024 describes a hair-setting polymer similar to that in JP-A-03206023, which additionally comprises from 5 to 50% by weight of an N-alkyl-substituted acrylamide. The hair-setting polymers described in both of these documents have a high content of hydrophobic monomers. Their wash-off is therefore in need of improvement.

DE-A-39 01 325 and DE-A-42 14 305 describe hair-setting compositions which comprise, as film former, a copolymer based on tert-butyl (methy)acrylate and (meth) acrylic acid, where the carboxyl groups of the copolymers have been partially or completely neutralized by amines. Here, the amines are chosen from mono-, di- or trialkanolamines, alkanediolamines or primary, secondary or tertiary alkylamines. Films based on these polyacrylates are generally hard and do not exhibit flexibility and, particularly with regard to their setting action, are in need of improvement.

DE-A-197 09 277 describes polysiloxane-containing hair setting compositions based on carboxyl-containing polymers, polysiloxanes having primary, secondary or tertiary amino groups, and low molecular weight neutralizing agents. The use of siloxanediamines which have not been further functionalized in hair setting compositions leads to crosslinked products which are difficult to wash out. Because of poor adhesion, the setting action of these formulations is in need of improvement.

U.S. Pat. No. 4,761,273 relates to mixtures of an anionic and a cationic polymer, where the anionic polymer is a polyacrylate or a derivative thereof, and the cationic polymer is a polyamine or a derivative thereof. These polymer salts are soft and more tacky than those according to the invention.

It is an object of the present invention to provide polymers. These should be suitable as a cosmetic composition, or for use in cosmetic compositions, in particular hair-treatment composition(s). Preferably, they should form films with good flexible properties and should be tack-free so that hair-treatment compositions based thereon impart elasticity to the hair. The polymers according to the invention should impart specific properties to the hair: natural hold, good combability, good feel and suppleness. This is the case particularly for polymers for hairspray formulations. For certain types of hair in the U.S.A. and Asia, polymers with increased flexibility are desired.

Surprisingly we have found that this object is achieved by certain polyureas and water-soluble or water-dispersible polymeric salts.

The present invention therefore relates to a polyurea constructed from:

a) a diamine which contains a group $—(—CH_2CH_2O—)_n—(C_3H_6—O—)_m$, where the order of the alkylene oxide units is arbitrary and m and n independently of one another are an integer between 0 and 50, and m+n is between 5 and 60, and b) at least one amino-containing or hydroxyl-containing polysiloxane and c) at least one diisocyanate, and d) optionally a di-, tri- or tetramine or polyamine which contains at least one inorganic group, and e) optionally one or more diamines having a molecular weight of from 60 to 6000 g/mol, where the polyurea contains at least one ionogenic or ionic group.

Preference is given to polyureas which contain at least one free amine group.

In addition, the invention relates to a process for the preparation of the abovementioned polyureas, where the polymerization is carried out in alcohol or water/alcohol solution at a temperature of less than or equal to 50° C. and, in the case of hydroxyl-containing polysiloxane, components b) and c) are firstly reacted with one another.

The invention further relates to the use of neutralized polyurea as film-forming auxiliary as additive for cosmetic preparations. In addition, the invention relates to the use of polyurea having ionic or ionogenic groups as neutralizing agents for polymers which contain ionic or ionogenic groups.

The invention relates to water-dispersible salts comprising

A) a base polymer which contains an ionic or ionogenic group, and

B) a neutralizing polymer which partially neutralizes the ionic or ionogenic group of the base polymer A, where the ionogenic or ionic groups of A are more frequent by a factor of from 2 to 30 than the ionogenic groups of the neutralizing polymer B.

Both the base polymer and the neutralizing polymer can be (partially) neutralized by adding neutralizing agents. As a rule, in this connection, the base polymer is firstly (partially) neutralized by adding a neutralizing agent, and then the neutralizing polymer is added. It is also possible to add the neutralizing polymer to the base polymer and then to neutralize with neutralizing agents. Particular preference is given to the (partial) neutralization of the base polymer and the subsequent addition of the neutralizing polymer. The neutralizing agent used is preferably a mixture of different neutralizing agent.

In a preferred embodiment, the base polymer A and/or the neutralizing polymer B is a polyurea or a polyurethane. In a particularly preferred embodiment, the base polymer A and/or the neutralizing polymer B is a polyurea as claimed in claim 1.

Neutralizing agents which can be used are: If anionogenic or ionic groups are present in excess, neutralization is carried out with an amine or amine mixture (e.g. amino-2-methylpropanol AMP, ethylenediamine etc.) and/or with a base (NaOH, KOH etc.).

Preferably, polymers with anionogenic groups are neutralized using mixtures which contain at least an amine, preferably a hydroxyl-containing amine, such as amino-2-methylpropanol, mono-, di- and triethanolamine, or a diamine, such as ethylenediamine, and an alkali metal hydroxide, preferably potassium hydroxide. Polyurethanes with anionogenic groups are preferably further neutralized using mixtures which contain at least one amine and an amino alcohol, preferably 2-amino-2-methyl-1-propanol.

If cationogenic or cationic groups are present in excess, neutralization is carried out with an acid or acid mixture (e.g. lactic acid, phosphoric acid etc.).

The amines, acids and/or bases are preferably cosmetically compatible.

An amine value of less than the acid number is particularly preferred.

Cosmetically compatible acids and polyacids are known to the person skilled in the art and are listed, for example, in WO 97/17052 and are incorporated herein. Cosmetically compatible amines are likewise known to the person skilled in the art and are also listed in the present application.

The base polymer A can be a polyurethane, polyurea or poly(urethane/urea) constructed from:
f) at least one compound which contains two (or more) active hydrogen atoms per molecule,
g) at least one compound which contains two active hydrogen atoms per molecule and has a molecular weight of from 56 to 300 g/mol,
h) at least one phosphate-, phosphonate-, carboxylate-, sulfate-, and/or tert-amine-containing compound or compounds thereof which contain the free acids that contain two active hydrogen atoms per molecule, and
i) at least one diisocyanate.

Or the base polymer A is a polyacrylate constructed from:
at least one $C_1$–$C_4$-alkylacrylic ester or $C_1$–$C_4$-alkylmethacrylic ester or acrylamide or methacrylamide or $C_1$–$C_4$-alkylacrylamide or $C_1$–$C_4$-alkylmethacrylamide,
at least one COOH-containing monomer.

Preference is given to polyacrylates comprising 65–90% by weight of ester or amide and 10–35% by weight of COOH-containing monomer.

The preferred esters are $C_4$-alkylacrylic esters or $C_4$-alkylmethacrylic ester.

The preferred amides are $C_4$-alkylacrylamides or $C_4$-alkylmethacrylamides.

The neutralizing polymer used is preferably a film-forming polymer which is dispersible with water.

The invention further relates to polyurethane, poly (urethane-urea) or polyurea or neutralizing polymer B, constructed from:
j) at least one compound or a mixture of compounds having at least two active hydrogen atoms per molecule and having a molecular weight of from 56 to 6000 g/mol, where at least one compound contains one of the following groups:
—(—$CH_2$—$CH_2$O—)m—($C_3H_6$O—)n—, where the order of the alkylene oxide units is arbitrary, and m and n independently of one another are an integer from 0 to 50, and the sum m+n is in the range from 5 to 60,
—$COO^-$, —$SO_3^-$ or
—$N^+$ group (quanternized amines),
k) optionally a compound having at least two active hydrogen atoms per molecule and at least one ionogenic group,
l) at least one amino-containing poly(dimethylsiloxane) and
m) at least one diisocyanate,
where the acid value or amine value is not greater than 60.

In this neutralizing polymer, the components are preferably present in the following amounts:
j) 10 to 90% by weight, preferably 15 to 80% by weight,
k) 0 to 20% by weight, preferably 0 to 10% by weight,
l) 0.1 to 30% by weight, preferably 0.3 to 20% by weight,
m) 5 to 30% by weight,
based on j+k+l+m.

In a preferred embodiment of the invention, the neutralizing polymer is constructed from at least one vinyllactam and/or at least one vinylamide and at least one amine-containing monomer, the amine value being between 1 and 60.

In particular, such a neutralizing polymer can be constructed from:
a) 25 to 80% by weight of at least one vinyllactam and/or vinylamide, preferably vinylpyrrolidone and/or vinylcaprolactam,
b) 1 to 20% by weight of at least one amine-containing monomer,
c) 0 to 40% by weight of a $C_1$–$C_4$-alkylacrylic ester or $C_1$–$C_4$-alkylmethacrylic ester or acrylamide or methacrylamide or $C_1$–$C_4$-alkylacrylamide or $C_1$–$C_4$-alkylmethacrylamide, preferably a corresponding $C_4$-alkyl ester and $C_4$-alkylamide,
where the amine value is between 1 and 60.

In a further preferred embodiment, the neutralizing polymer is constructed from at least one $C_1$–$C_{18}$-allylmethacrylic ester and/or $C_1$–$C_{18}$-alkylmethacrylamide and at least one amine-containing and/or COOH-containing monomer.

The invention also relates to processes for the preparation of the abovementioned polymeric salts, where the base polymer is partially neutralized in a suitable solvent (water or alcohol/water) with a monovalent neutralizing agent, and then the neutralizing polymer is added.

Preference is given to a process for the preparation of a polymeric salt in which a vinyllactam-carrying polymer is used as neutralizing polymer, where an anionic or ionogenic base polymer (preferably one carrying carboxylate groups) is preferably neutralized at a temperature of about 80° C. for about 1 h in water or alcohol/water, and is then neutralized with a low molecular weight amine. The organic solvents can be removed after the addition of water, for example by distillation under reduced pressure. The aqueous solution or dispersion of the polymeric salt can be used to obtain the polymeric salt (e.g. by spray drying).

The polymeric salts according to the invention are at least partially crosslinked. The crosslinking here is via ionic bonding between anionic groups of at least two different polymer chains of a polymer(base or neutralizing polymer) and at least two cationic groups of the other polymer (neutralizing or base polymer).

The amines always have at least two primary, secondary and/or tertiary amino groups which are able to form cationic groups.

Component f) of the base polymer based on polyurethanes is preferably a polymer having a number-average molecular weight in the range from about 300 to 5000, preferably from about 400 to 4000, in particular from 500 to 3000 g/mol. Polymers f) which can be used are, for example, polyester diols, polyetherols, polyamidediamines, polysiloxane polyol/polyamines and mixtures thereof. Polyetherols are preferably polyalkylene glycols, e.g. polyethylene glycols, polypropylene glycols, polytetrahydrofurans etc., copolymers of ethylene oxide and propylene oxide or block copolymers of ethylene oxide, propylene oxide and butylene oxide which contain the copolymerized alkylene oxide units in random distribution or in the form of blocks. Also suitable are α,ω-diamino polyethers, which can be prepared by amination of polyalkylene oxides with ammonia. Preference is given to using polyester-diols and mixtures which contain these as component f).

Suitable polytetrahydrofurans can be prepared by cationic polymerization of tetrahydrofuran in the presence of acidic catalysts such as, for example, sulfuric acid or fluorosulfuric acid. Such preparation processes are known to the person skilled in the art.

Preferred polyester-diols have a number-average molecular weight in the range from about 400 to 5000, preferably 500 to 3000, in particular 600 to 2000.

Suitable polyester-diols are all those which are customarily used for the preparation of polyurethanes, in particular those based on aromatic dicarboxylic acids, such as terephthalic acid, isophthalic acid, phthalic acid, Na or K sulfoisophthalic acid etc., on aliphatic dicarboxylic acids, such as adipic acid or succinic acid etc., and an cycloalphatic dicarboxylic acids, such as 1,2-, 1,3- or 1,4-cyclohexanedicarboxylic acid. Suitable diols are particularly aliphatic diols, such as ethylene glycol, propylene glycol, 1,6-hexandediol, neopentyl glycol, diethylene glycol, polyethylene glycols, polypropylene glycols, 1,4-dimethylolcyclohexane.

Preference is given to polyester-diols based on aromatic and aliphatic dicarboxylic acids and aliphatic diols, in particular those in which the aromatic dicarboxylic acid makes up from 10 to 95 mol %, in particular from 40 to 90 mol %, of the total dicarboxylic acid content (remainder is aliphatic dicarboxylic acids).

Particularly preferred polyester-diols are the reaction products of phthalic acid and diethylene glycol,
isophthalic acid/adipic acid and 1,6-hexanediol and/or neopentyl glycol,
isophthalic acid/adipic acid and 1,4-dimethylolcyclohexane and/or neopentyl glycol,
isophthalic acid/adipic acid and 1,4-dimethylolcycohexane and/or dimethylolcyclohexane and/or diethylene glycol,
adipic acid and 1,6-hexanediol and/or neopentyl glycol and/or 1,4-dimethylolcyclohexane and/or diethylene glycol,
polyamidediamine, in particular diamine of itaconic acid/aliphatic diamines, e.g. itaconic acid/hexanediamine (1,6).

The polysiloxanes are preferably a compound of the formula I

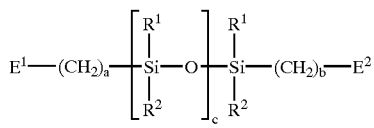

(I)

in which
$R^1$ and $R^2$ independently of one another are $C_1$–$C_4$-alkyl, benzyl or phenyl,
$E^1$ and $E^2$ independently of one another are OH or $NHR^3$, where $R^3$ is hydrogen, $C_1$- to $C_6$-alkyl or $C_5$- or $C_8$-cycloalkyl,
a and b independently of one another are from 2 to 8,
c is from 3 to 50,
and mixtures thereof.

In the amino-containing polysiloxanes, at least $E^1$ or $E^2$ is $NHR^3$.

In the hydroxyl-containing polysiloxanes, at least $E^1$ or $E^2$ is —OH.

Suitable alkyl radicals are, for example, methyl, ethyl, n-propyl, isopropyl, n-butyl, t-butyl, n-pentyl, n-hexyl etc. Suitable cycloalkyl radicals are, for example, cyclopentyl, cyclohexyl, cycloheptyl, cyclooctyl etc.

Preferably, $R^1$ and $R^2$ are both methyl.

These polysiloxanes preferably have a number-average molecular weight in the range from about 300 to 5000, preferably 400 to 3000.

The polysiloxanes are furthermore preferably a compound of the formula II

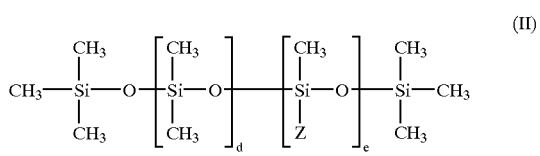

(II)

in which
the order of the siloxane units is arbitrary,
d is a value from 5 to 200, preferably 10 to 100,
e is a value from 1 to 20, preferably from 2 to 10,
Z is a radical of the formula —$(CH_2)_f$—$NH_2$ in which f is a number from 1 to 10, preferably from 2 to 6, or
Z is a radical of the formula —$(CH_2)_g$—NH—$(CH_2)_h$—$NH_2$ in which g and h independently of one another are from 0 to 6, preferably 2 to 3, or
Z is $(CH_2)_f$—$(CH_2$—$CH_2O)_n$—$(C_3H_6O)_m$—H, in which n+m is in the range between 5 and 60, and m and n independently of one another are between 0 and 50.

These include, for example, the MAN and MAR brands from Degussa-Hüls and the Finish brands from Wacker, e.g. Finish WT 1270 and Belsil 6031 from Wacker.

Suitable polysiloxanes are also the polydimethylsiloxanes described in EP-A227 816, to which reference is hereby made.

Suitable diamines are, for example, ethylenediamine, propylenediamine, 1,4-diaminobutane, 1,5-diaminopentane and 1,6-diaminohexane.

Suitable polyamines are compounds of the following formula:

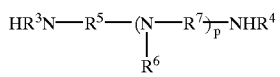

in which
p is an integer from 0 to 4,
$R^3$ and $R^4$ independently of one another are hydrogen, $C_1$- to $C_{40}$-alkyl or $C_6$- to $C_{40}$-alkenyl, where the alkyl and alkenyl radicals can carry at least one inorganic and/or ionic group which is chosen from —COOY, —$SO_3Y$ and —$PO_3Y$, where Y is H, Li, Na, K or ammonium, where, when p=0, at least one of the radicals $R^3$ or $R^4$ is a $C_1$- to $C_{40}$-alkyl or $C_6$- to $C_{40}$-alkenyl radical which carries at least one ionogenic and/or ionic group,
$R^5$ and $R^7$ are a $C_2$- to $C_6$-alkylene radical, where, when p is >1, the radicals $R^7$ are independently chosen from $C_2$- to $C_6$-alkylene radicals,
$R^6$ is $C_1$- to $C_6$-alkyl, $C_5$- to $C_8$-cycloalkyl, phenyl or phenyl-$C_1$–$C_4$-alkyl, where, when p is >1, the radicals $R^6$ are independently chosen from these meanings.

If the polyamine of the above formula has two or more repeat units –(N($R^6$)—$R^7$)$_p$, then these can have identical or different meanings.

Preferably, p is 1, 2 or 3, in particular 1 or 2.

When p is 0, then the radicals $R^3$ and $R^4$ are independently preferably a $C_1$- to $C_{40}$-alkyl or $C_6$- to $C_{40}$-alkenyl radical, each of which carries at least one ionogenic and/or ionic group.

Preferably, $R^3$ and $R^4$ independently of one another are hydrogen, $C_1$- to $C_{30}$-alkyl, preferably $C_1$- to $C_{12}$-alkyl, in particular $C_1$- to $C_8$-alkyl or a radical of the formula

—$(CH_2)_{2-6}$—$SO_3Y$, where Y is H, Li, Na, K or ammonium.

In particular, $R^3$ and $R^4$ independently of one another are hydrogen, methyl, ethyl, n-propyl, isopropyl, n-butyl, sec-butyl, tert-butyl, n-pentyl, h-hexyl. Specifically, $R^3$ and $R^4$ are both hydrogen.

Preferably, $R^5$ is a $C_2$- to $C_4$-alkylene radical.

Preferably, $R^6$ is methyl, ethyl, n-propyl, isopropyl, n-butyl, sec-butyl, tert-butyl, cyclohexyl, phenyl or benzyl.

Preferably, $R^7$ is a $C_2$- to $C_4$-alkylene radical.

The polyamine used is preferably diethylenetriamine, N-methyldiethylenetriamine, N-ethyldiethylenetriamine, N,N,N',N'-tetramethyldiethylenetriamine, N,N,N',N'-tetraethyldiethylenetriamine, dipropylenetriamine, N-methyldipropylenetriamine, N-ethyldipropylenetriamine, N,N'-bis(3-aminopropyl)butane-1,4-diamine, triethylenetetramine, tetraethylenepentamine and mixtures thereof. The polyamine is particularly preferably N-methyldipropylenetriamine.

Component g) of the base polymer having two active hydrogen atoms is preferably a diol, diamine, amino alcohol, or a mixture thereof. The molecular weight of these compounds is in a range from about 56 to 300. If desired, up to 3 mol % of said compounds can be replaced by triols or triamine.

Preference is given here to using diols. Diols which can be used are, for example, ethylene glycol, propylene glycol, butylene glycol, neopentyl, glycol, cyclohexanedimethylol, di-, tri-, tetra-, penta- or hexaethylene glycol and mixtures thereof. Preference is given to using neopentyl glycol and/or cyclohexanedimethylol.

Suitable amino alcohols, are for example, 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol etc.

Suitable diamines are, for example, ethylenediamine, propylenediamine, 1,4-diaminobutane, 1,5-diaminopentane and 1,6-diaminohexane, and fatty diamines of the structure R—NH—$(CH_2)_{2-3}$—$NH_2$ where R=$C_8$–$C_{22}$-alkyl or $C_8$–$C_{22}$-alkenyl radical.

Suitable compounds h) of the base polymer have two active hydrogen atoms and at least one anionogenic and/or anionic group per molecule or at least one cationogenic and/or cationic group per molecule.

Preferred compounds having two active hydrogen atoms and at least one anionogenic and/or anionic group per molecule are, for example, compounds containing carboxylate and/or sulfonate groups. Particularly preferred components containing two active hydrogen atoms are 2,2-hydroxymethyl-substituted carboxylates, in particular dimethylolpropanoic acid and mixtures which contain dimethylolpropanoic acid.

Components containing two active hydrogen atoms which also can be used are compounds of the formula $H_2N(CH_2)_w$—NH—$(CH_2)_x$—$COO^-M^+$
$H_2N(CH_2)_w$—NH—$(CH_2)_x$—$SO_3^-M^+$ in which w and x independently of one another are an integer from 1 to 8, in particular 1 to 6, and M is Li, Na or K, and compounds of the formula $H_2N(CH_2CH_2O)_y(CH_2CH(CH_3)O)_z(CH_2)_w$—NH—$(CH_2)_x$—$SO_3^-$ $M^+$ in which w and x are as defined above, y and z independently of one another are an integer from 0 to 50, where at least one of the two variables y and z is >0. The order of the alkylene oxide units here is arbitrary. The last-named compounds preferably have a number-average molecular weight in the range from about 400 to 3000. A suitable compound of this type is, for example, Poly ESP 520 from Raschig.

If desired, the polyurethanes can, in addition to or instead of the compounds containing ionogenic and/or anionic groups, also contain, in incorporated form, compounds which have at least two active hydrogen atoms and at least one cationogenic and/or cationic group, preferably at least one nitrogen-containing group, per molecule. The nitrogen-containing group is preferably a tertiary amino group or a quaternary ammonium group. Preference is given, for example, to compounds to the formulae

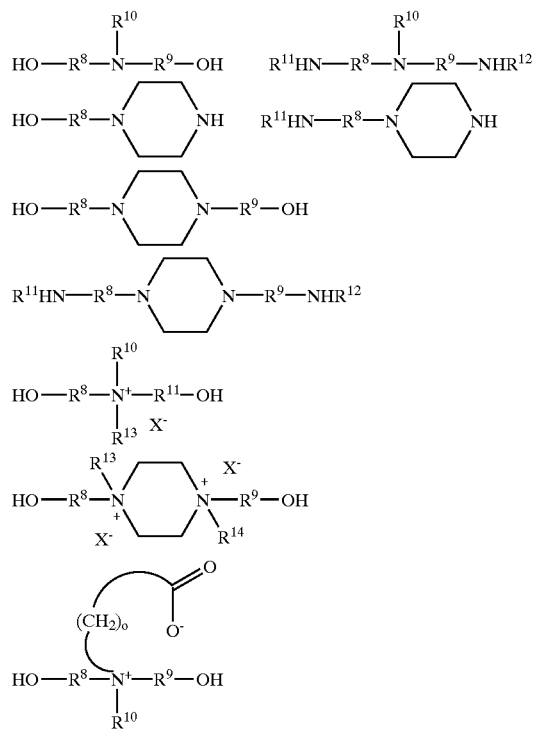

in which $R^8$ and $R^9$, which can be identical or different, are $C_2$–$C_8$-alkylene, $R^{10}$, $R^{13}$ and $R^{14}$, which can be identical or different, are $C_1$–$C_6$-alkyl, phenyl or phenyl-$C_1$–$C_4$-alkyl, $R^{11}$ and $R^{12}$, which can be identical or different, are H or $C_1$–$C_6$-alkyl, o is 1, 2 or 3, $X^-$ is chloride, bromide, iodide, $C_1$–$C_6$-alkylsulfate or $SO_4^{2-}/2$.

Particular preference is given to N-($C_1$–$C_6$-alkyl) diethanolamines, such as methyldiethanolamine or N-alkyldialkylenetriamine, such as N-methyldipropylenetriamine.

The diisocyanate component (component c), i) and m)) is a customary aliphatic, cycloaliphatic and/or aromatic diisocyanate, such as tetramethylene diisocyanate, hexamethylene diisocyanate, methylenediphenyl diisocyanate, tolylene 2,4- and 2,6-diisocyanate and their isomeric mixtures, o-, m- and p-xylylene diisocyanate, 1,5-naphthylene diisocyanate, 1,4-cyclohexylene diisocyanate, dicyclohexylmethane diisocyanate and mixtures thereof, in particular isophorone diisocyanate, hexamethylene diisocyanate and/or dicyclohexylmethane diisocyanate. If desired, up to 3 mol % of said compounds can be replaced by triisocyanates.

As is customary for the preparation of polyurethanes and polyureas, it is possible to use chain extenders. Suitable chain extenders are, for example, hexamethylenediamine, piperazine, 1,2-diaminocyclohexane, 1,3-diaminocyclohexane, 1,4-diaminocyclohexane, neopentanediamine and 4,4'-diaminodicyclohexylmethane.

The polyurethanes and polyureas described are preferably obtainable by reacting the reactants for the diisocyanates with the diisocyanates under an inert-gas atmosphere in an inert solvent, e.g. methyl ethyl ketone in the case of compounds containing OH groups, and water or an alcohol such as ethanol in the case of compounds containing NH groups, at temperatures of from 30° C. to 110° C., preferably at 40° C. to 100° C. in the case of compounds containing OH group and below 50° C., preferably at 5° C. to 30° C. in the case of compounds containing NH groups. This reaction can optionally be carried out in the presence of chain extenders in order to prepare polyurethanes or polyureas with higher molecular weights. The reaction can be accelerated by adding catalysts such as organotin compounds, e.g. dibutyltin dilaurate, tetraalkyl titanates in particular in the case of reactants containing OH groups. As is customary in the preparation of polyurethanes, the reactants for the diisocyanates and the diisocyanates themselves are expediently used in the molar ratio from 0.8 to 1.1:1.

The reaction can, in the case of polyurethanes, be carried out without solvent or in a suitable inert solvent or solvent mixture. Suitable solvents are aprotic polar solvents, e.g. tetrahydrofuran, ethyl acetate, N-methylpyrrolidone, dimethylformamide and, preferably, ketones, such as acetone and methyl ethyl ketone. The reaction is preferably carried out under an inert-gas atmosphere, such as, for example, under nitrogen. In addition, the reaction preferably takes place at ambient pressure or under increased pressure. The components are preferably used in amounts such that the ratio of NCO equivalent of the compounds of the diisocyanate to equivalent of active hydrogen atom of the other components is in a range from about 0.6:1 to 1.4:1, preferably from 0.8:1 to 1,2:1, in particular from 0.9:1 to 1.1:1. If necessary, any free isocyanate groups which are still present in the polyurethanes can be deactivated by subsequent reaction with amines, preferably aminoalcohols. Suitable means and aminoalcohols are those mentioned above, preferably 2-amino-2-methyl-1-propanol or tert-amine-containing diamine, such as N,N-dimethylaminopropyldiamine.

The polyurethanes and polyureas described are, because of their ionogenic groups, in particular when charges are present, usually readily alcohol- and water-soluble or at least dispersible in alcohol and water without the assistance of emulsifiers. The alcohols intended here are, in particular, short-chain $C_1$–$C_4$-alkanole such as methanol, ethanol, isopropanol or n-propanol. Charged cationic groups can be produced in the polyureas from the tertiary amine nitrogen atoms present either by protonation, e.g. using phosphoric acid or carboxylic acid such as lactic acid, or by quaternization, e.g. using alkylating agents such as $C_1$- to $C_4$-alkyl halides or $C_1$- to $C_4$-alkyl sulfates. Examples of such alkylating agents are ethyl chloride, ethyl bromide, methyl chloride, methyl bromide, dimethyl sulfate and diethyl sulfate. The anionic or anionogenic groups are present in the corresponding amine. Since some of the polyurethanes and polyureas described are novel substances, the present invention further relates to these novel substances.

By neutralization of anionogenic groups of different base polymers A) by an amino group of each amine (neutralizing agent), at least some of the polymer chains are crosslinked, with salt formation.

Suitable neutralizing agents for the (partial) neutralization of the anionogenic base polymers are all the amines listed under the neutralizing agents; these can be used in each case individually or in the form of mixtures. To neutralize the anionogenic groups of the base polymers, it is also possible to use mixtures which contain at least one amine and at least one other base. Suitable other bases for the neutralization of the polymers are alkali metal bases, such as sodium hydroxide solution, potassium hydroxide solution, sodium carbonate, potassium carbonate, sodium hydrogencarbonate, potassium hydrogencarbonate and alkaline earth metal bases, such as calcium hydroxide, calcium oxide, magnesium hydroxide or magnesium carbonate, and ammonia and amines which do not form a counterion B.

If the base polymer used is a polyurethane, poly(urethaneurea) or polyurea which additionally has amino groups as cationogenic groups, then these can be partially or completely converted into the corresponding cationic groups by neutralization with an acid such as lactic acid or phosphoric acid, or by quaternization. Polyurethanes, poly(urethaneurea) or polyurea which have both cationogenic and anionogenic groups can be successively subjected to neutralization with at least one acid, neutralization with at least one base and if desired additionally quaternization. The order of the neutralization steps is generally arbitrary in this case.

If desired, cationogenic groups can also be partially or completely quaternized. The quaternization can, for example, be carried out using alkylating agents, such as $C_1$- to $C_4$-alkyl halides or sulfates. Preferred alkylating agents are ethyl chloride, ethyl bromide, methyl chloride, methyl bromide, dimethyl sulfate and diethyl sulfate.

The proportion of the polymeric salt in the neutralizing polymer is preferably at least about 1% by weight, in particular at least 3% by weight.

Preferably, the proportion of the polymeric salt in the neutralizing polymer is at most about 50% by weight, preferably at most about 40% by weight.

The water-soluble or water-dispersible polymeric salts according to the invention are obtainable by reaction of the base polymers, containing ionogenic and/or anionic groups bonded to the polymer chain, with at least one neutralizing polymer. The reaction can preferably be carried out immediately after the preparation of the base polymers and is generally carried out in the same reaction vessel. If desired, for preparation of the salts according to the invention, it is also possible to use a base polymer which has been prepared separately or which is commercially available. Suitable polyurethanes are described, for example, in DE-A-42 41 118, DE-A-42 25 045 and EP-A 0 619 111, to the entire contents of which reference is made. Suitable acrylate copolymers are described, for example, in DE-A-39 01 325 and De-A-43 14 305, to the entire contents of which reference is made. Suitable solvents for the reaction are those mentioned above for the preparation of the polyurethanes.

The neutralization of base polymers containing acid groups can be carried out by adding a base or a base mixture.

If, in the preparation of the polymeric salts, a water-miscible organic solvent is used, then this can be removed immediately afterward by customary processes known to the person skilled in the art, e.g. by distillation at reduced pressure. Prior to removing the solvent, water can be additionally added to the polymeric salt. Replacement of the solvent by water gives a solution or dispersion of the polymeric salt, from which, if desired, the polymeric salt can be obtained in the usual manner, e.g. by spray drying.

The pH of the aqueous solutions or dispersions of the polymeric salts can be adjusted by adding an acid or base. Suitable acids and bases are those mentioned above as additional neutralizing agents. Preferably, the pH for anionic polymeric salts is in the alkaline range, in particular >7.5. The pH for cationic polymeric salts is preferably in the acidic range, in particular from 5.5 to 6.5.

The polymeric salts according to the invention are water-soluble or water-dispersible. They generally form clear and tack-free films and can be washed out very easily with water. Advantageously, the polymeric salts according to the invention also give films with very good elasticity. This is generally higher than the elasticity which is usually obtained for polyurethanes known from the prior art using short-chain neutralizing agents.

For the purposes of the present invention, the terms "alkyl" and "alkylene" include straight-chain and branched alkyl or alkylene groups. These are preferably straight-chain or branched, $C_1$- to $C_{40}$- and, particularly preferably, $C_2$- to $C_{30}$-alkyl and alkylene groups.

$C_1$- to $C_6$-alkyl is preferably methyl, ethyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl etc.

$C_2$- to $C_6$-alkylene stands for straight and branched $C_2$- to $C_6$-alkylene radicals, preferably $C_2$- to $C_4$-alkylene radicals. These preferably include ethylene, propylene, propane-1,3-diyl, butane-1,4-diyl, butane-1,3-diyl, butane-1,2-diyl, butane-2,3-diyl, 2-methylpropane-1,3-diyl, pentane-1,5-diyl, pentane-1,4-diyl, pentane-1,3-diyl, pentane-1,2-diyl, 1-methylbutane-1,4-diyl, 2-methylbutane-1,4-diyl, hexane-1,6-diyl, hexane-1,5-diyl, hexane-1,4-diyl, hexan-1,3-diyl, hexan-1,2-diyl etc.

$C_6$- to $C_{40}$-alkenyl preferably stands for straight and branched alkylene groups which can be mono-, di- or polyunsaturated. It is preferably $C_9$- to $C_{35}$-, in particular $C_{10}$- to $C_{30}$- and specifically $C_{12}$- to $C_{26}$-alkenyl groups. These include, in particular, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, linolyl, linolenyl, elaostearylyl etc.

The aniogenic groups are carboxylic acid groups and/or sulfonic acid groups and/or phosphate and/or phosphonate groups.

The anionic groups are preferably carboxylate and/or sulfonate groups. As counterion, these preferably have an alkali metal, in particular Na or K, or an ammonium ion derived from ammonia or a primary, secondary or tertiary amine which is different to the amines used as neutralizing agents.

The cationic groups are primary, secondary and, particularly, tertiary amines. Cationic groups are the protonation and/or quaternization product of an amine and, preferably, the product of the reaction with a mineral acid, such as hydrochloric acid or sulfuric acid, or the product of the reaction with a quaternizing agent. The customary alkylating agents are suitable for the quaternization.

The quaternizing agents introduce a $C_1$–$C_6$-alkyl, $C_5$–$C_8$-cycloalkyl, phenyl, phenyl-$C_1$–$C_4$-alkyl.

Suitable N-vinylamides are N-vinylformamide, N-vinylacetamide, N-vinylpropionamide etc. Preference is given to using N-vinylformamide.

Suitable N-vinyllactams and derivatives thereof are those which can have, for example, one or more $C_1$–$C_6$-alkyl substituents, such as methyl, ethyl, n-propyl, isopropyl, n-butyl, sec-butyl, tert-butyl etc. These include, for example, N-vinylpyrrolidone, N-vinylpiperidine, N-vinylcaprolactam, N-vinyl-5-methyl-2-pyrrolidone, N-vinyl-5-ethyl-2-pyrrolidone, N-vinyl-6-methyl-2-piperidine, N-vinyl-6-ethyl-2-piperidine, N-vinyl-7-methyl-2-caprolactam, N-vinyl-7-ethyl-2-caprolactam etc.

Suitable amine-containing monomers are, for example, those of the following formula

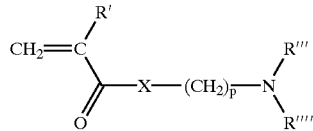

where
R'=H, $CH_3$
X=O, NH
R''', R''''=are identical or different and can represent $CH_3$, —$C_2H_5$, —$C_3H_7$, —$C_4H_9$, -tert-$C_4H_9$,
p=1 to 5

Particularly suitable monomers are:
N,N-Dimethylaminoethyl (meth)acrylate
N,N-Dimethylaminopropyl (meth)acrylate
N,N-Dimethylaminoethyl (meth)acrylamide
N,N-Dimethylaminopropyl (meth)acrylamide.

Very particularly suitable monomers are:
N,N-Dimethylaminoethyl methacrylate
N,N-Dimethylaminoethyl methacrylamide
N,N-Dimethylaminopropyl methacrylamide.

Suitable COOH-containing monomers are, for example, α-,β-ethylenically unsaturated mono- and dicarboxylic acids, such as, for example, acrylic acid, methacrylic acid, fumaric acid, maleic acid, itaconic acid, crotonic acid and mixtures thereof. Preference is given to using acrylic acid, methacrylic acid and mixtures thereof.

The polymeric salts according to the invention and the polyureas according to the invention (summarized under the term polymers according to the invention) are particularly highly suitable as or in (a) hair-setting polymer(s) which impart flexibility to the hair.

The polymers according to the invention are suitable as auxiliaries in cosmetics. The invention therefore further relates to the use of the polymers according to the invention in cosmetic compositions, in particular as film formers and/or coating compositions and/or binders. In this connection, their use is possible, in particular in cosmetic compositions for the treatment of keratin-containing and keratin-analogous surfaces such a hair, skin and nails. They are particularly suitable for hair cosmetics, preferably as setting polymers in hairsprays, setting foams, hair mousse, hair gel and shampoos. They are furthermore preferably suitable for use in pigment-containing cosmetic compositions, such as in decorative cosmetics, in particular in mascara and eyeshadows. They are also suitable for the preparation of stick-shaped cosmetic products, such as deodorant sticks, make-up sticks, etc.

The polymers according to the invention are also suitable as auxiliaries in pharmacy, preferably as or in coating composition(s) or binder(s) for solid medicament forms. The invention therefore further relates to the use of the polymers according to the invention in pharmaceutical compositions, in particular as film formers and/or coating compositions and/or binders. Thus, the abovementioned polymers can be used as tablet coatings and tablet binders.

The polymers according to the invention are also preferably suitable for use as or in coating composition(s) for the textile, paper, printing, leather and adhesives industry.

The polymers according to the invention are suitable as constituent, as active polymer, film former, coating, binder, (co)emulsifier, penetration inhibitor, crystallization inhibitor, moisture-retention additives.

The polymers according to the invention are also suitable as viscosity-regulating agents. Particularly in the case of oil- and water-containing cosmetic compositions, such ask, for example, creams or lotions, it is possible, depending on the respective oil and water content, to adjust the viscosity to the desired value in a targeted manner by adding the polymers according to the invention.

The invention further relates to a cosmetic and/or pharmaceutical composition which comprises at least one polymer according to the invention (=polyurea as claimed in claim 1 or polymeric salt). The composition generally comprises the polymers according to the invention in an amount in the range from about 0.2 to 30% by weight, in particular from 0.5 to 20% by weight, based on the total weight of the composition.

If the polymers according to the invention used in the compositions according to the invention are water-dispersible, they can be used in the form of aqueous dispersions having particle diameters of customarily from 1 to 350 nm, preferably from 1 to 250 nm. The solids contents of the preparations are usually in a range from about 0.2 to 30, in particular from 0.5 to 20% by weight, preferably from 1 to 12% by weight. These microdispersions do not generally require emulsifiers or surfactants for their stabilization.

The compositions according to the invention can preferably be in the form of a hair-treatment composition, such as setting foam, hair mousse, hair gel, shampoo and, in particular, in the form of a hairspray. For use as conditioning polymer or setting polymer, preference is given to compositions which comprise the polymers according to the invention whic have at least one glass transition temperature $T_g \geq 10°$ C., preferably $\geq 20°$ C. The K value of these polymers (measured in accordance with E. Fikentscher, Cellulose-Chemie 13 (1932), p. 58–64) using a 1% strength by weight solution in N-methylpyrrolidone is preferably in a range from 23 to 90, in particular from 25 to 60.

If the polymeric salts according to the invention have siloxane groups, then the siloxane content of these polymers is generally from 0.05 to 20% by weight, based on the total weight of the incorporated components.

The cosmetic compositions according to the invention are preferably hair-treatment compositions. These are usually in the form of an aqueous dispersion or in the form of an alcoholic or aqueous-alcoholic solution. Examples of suitable alcohols are ethanol, propanol, isopropanol etc.

Furthermore, the hair-treatment compositions according to the invention can generally comprise customary cosmetic auxiliaries, for example plasticizers, such as glycerol and glycol; emollients; perfumes, surfactants, UV absorbers; dyes, antistatics; agents for improving combability; preservatives; and antifoams.

If the cosmetic compositions according to the invention are formulated as hairspray, they comprise a sufficient amount of a propellant, for example a low-boiling hydrocarbon or ether, such as propane, butane, isobutane or dimethyl ether. Other propellants which can be used are compressed gases, such as nitrogen, air or carbon dioxide. The amount of propellant can thus be kept low, in order not to increase the VOC content unnecessarily. It is then generally no more than 55% by weight, based on the total weight of the composition. However, higher VOC contents of 85% by weight and above are also possible, if desired.

The polymers according to the invention can also be used in combination with other polymers in the compositions. The polymers according to the invention are therefore also suitable for improving the elasticity of traditional hair-treatment compositions, in particular hair-setting compositions. These then impart very good flexibility and suppleness to the hair.

Such other polymers are, in particular:

nonionic, water-soluble or water-dispersible polymers or oligomers, such as polyvinylcaprolactam, e.g. Luviskol Plus (BASF), or polyvinylpyrrolidone and copolymers thereof, in particular with vinyl esters, such as vinyl acetate, e.g. Luviskol VA 37 (BASF); polyamides, e.g. based on itaconic acid and aliphatic diamines;

amphoteric or switterionic polymers, such as the octylacrylamide/methyl methacrylate/tert-butylaminoethyl methacrylate/2-hydroxypropyl methacrylate copolymers obtainable under the names Amphomer® (National Starch), and switterionic polymers, as disclosed, for example, in German Patent Applications DE39 29 973, DE 21 50 557, DE 28 17 369 and DE 37 08 451. Acrylamidopropyltrimethylammonium chloride/acrylic acid or methacrylic acid copolymers and their alkali metal and ammonium salts are preferred switterionic polymers. Other suitable switterionic polymers are methacrylethylbetain/methacrylate copolymers, which are available commercially under the name Amersette® (AMERCHOL), and copolymers of hydroxyethyl methacrylate, methyl methacrylate, N,N-dimethylaminoethyl methacrylate and acrylic acid (Jordapon®);

anionic polymers, such as vinyl acetate/crotonic acid copolymers, as are sold, for example, under the names Resyn® (NATIONAL STARCH), Luviset® (BASF) and Gafset® (GAF) vinylpyrrolidone/vinyl acrylate copolymers, obtainable for example under the trade name Luviflex® (BASF). A preferred polymer is the vinylpyrrolidone/acrylate terpolymer obtainable under the name Luviflex® VBM-35 (BASF). Acrylic acid/ethyl acrylate/ N-tert-butylacrylamide terpolymers, which are sold, for example, under the name Ultrahold® strong (BASF), and Luvimer® (BASF, terpolymer of t-butyl acrylate, ethyl acrylate and methacrylic acid), sodium sulfonate-containing amides or sodium sulfonate-containing polyesters, or cationic (quaternized) polymers, e.g. cationic polyacrylate copolymers based on N-vinyllactams and their derivatives (N-vinylpyrrolidone, N-vinylcaprolactam etc.), and customary cationic hair conditioning polymers, e.g. Luviquat® (copolymer of vinylpyrrolidone and vinylimidazolium methochloride), Luviquat® Hold (copolymer of quaternized N-vinylimidazole, N-vinylpyrrolidone and N-vinylcaprolactam), Merquat® (polymer based on dimethyldiallylammonium chloride), Gafquat® (quaternary polymers, which are formed by reaction of polyvinylpyrrolidone with quaternary ammonium compounds), polymer JR (hydroxyethylcellulose with cationic groups), polyquaternium grades (CTFA names) etc.;

nonionic, siloxane-containing, water-soluble or -dispersible polymers, e.g. polyether siloxanes, such as Tegopren® ((Goldschmidt) or Belsil® (Wacker).

The polymers according to the invention can be used in admixture with an amide-containing polymer. Examples thereof include the polyurethanes described in DE-A-42 25 045, the abovedescribed vinylpyrrolidone/acrylate terpolymers and acrylic acid/ethyl acrylate/N-tert-butylacrylamide terpolymers (e.g. Ultrahold® strong from BASF AG), the abovementioned amide-containing amphoteric polymers (e.g. Amphomer®) and in particular copolymers which have a proportion of amide-containing monomers, such as N-vinyllactams, of at least 30% by weight (e.g. Luviskol®plus and Luviskol®VA37 from BASF AG).

The other polymers are preferably present in amounts up to 10% by weight, based on the total weight of the composition.

A preferred hair-treatment composition comprises:

from 0.2 to 30, in particular from 0.5 to 20% by weight, preferably from 1 to 10% by weight, of at least one polymer according to the invention (polyurea as claimed in claim 1 and polymeric salts as claimed in claim 5), from 50 to 99.5% by weight, preferably from 55 to 99% by weight, of a solvent chosen from water and water-miscible solvents, preferably $C_2$- to $C_5$-alcohols, in particular ethanol, and mixtures thereof, from 0 to 70% by weight, preferably from 0.1 to 50% by weight, of a propellant, The propellant used is usually propane/butane, preferably dimethyl ether, from 0 to 10% by weight, preferably from 0.1 to 10% by weight, of at least one water-soluble or -dispersible polymer which is different from the polymers according to the invention, from 0 to 0.5% by weight, preferably from 0.001 to 2% by weight, of at least one water-soluble or water-dispersible silicone compound.

The composition according to the invention can comprise, as silicone compound, at least one nonionic, siloxane-containing, water-soluble or -dispersible polymer, in particular chosen from the abovementioned polyether siloxanes. The proportion of this component is then generally from about a 0.001 to 2% by weight, based on the total weight of the composition.

The composition according to the invention can comprise, as additional component, at least one water-insoluble silicone, in particular a polydimethylsiloxane, e.g. the Abil® grades from Goldschmidt. The proportion of this component is then generally from about 0.0001 to 0.2% by weight, preferably from 0.001 to 0.1% by weight, based on the total weight of the composition.

The composition according to the invention can optionally additionally comprise an antifoam, e.g. based on silicone. The amount of the antifoam is then generally up to about 0.001% by weight, based on the total amount of the composition.

In addition to the abovementioned components, the composition according to the invention preferably comprises:

from 0 to 40% by weight, preferably from 0.1 to 35% by weight, of at least one surfactant, from 0 to 5.0% by weight of an emulsifier, from 0 to 3% by weight, preferably from 0.05 to 2.5% by weight, of at least one salt, from 0 to 3% by weight, preferably from 0.05 to 2.5% by weight, of at least one thickener, and optionally other customary additives. Other additives which may be mentioned are: dyes, pigments, UV absorbers (each of which can be used in amounts from 0 to 5.0% by weight), and preservatives and perfumes. These are then generally present in each case in an amount of from about 0 to 0.2% by weight, preferably from 0.001 to 0.2% by weight.

All of the stated weight data relate to the total weight of the composition.

The compositions according to the invention have the advantage that, on the one hand, they impart the desired hold to hair and the polymers can be readily washed out (are redispersible), and, on the other hand, the hair remains elastic, supple and tack-free.

The invention is illustrated in more detail by reference to the following, nonlimiting examples.

EXAMPLES

The assessment of the flexibility of the polymers was determined as follows:

Strips of from 2 to 5 mm in width are stamped out of a 20% strength polymer solution having a layer thickness of from 90 to 140 $\mu$m, and tested for feel, strength and flexibility. In the test for tackiness, clarity and wash-off, a glass plate is coated with the films for the testing.

For the valuation, either a 20% strength ethanolic solution is coated onto PE film and dried to give a 500 $\mu$m film.
elasticity: brittle (4)/hard (3)/moderate (2)/very soft (1)
tensile strength: flowing (4)/poor (3)/moderate(2)/solid (1)
feel: rough, impeding (4)/impeding(3)/good (2)/supple-smooth (1)

or a 5% strength aqueous ethanolic solution is coated on glass plates to give films
tackiness: tacky (4)/slightly tacky (3)/satisfactory (2)/non-tacky (1)
wash-off: insoluble (4)/poor (3)/satisfactory (2)/clear (1)

Examples 1 to 4

Preparation of neutralizing polymers

The neutralizing polymer is either polymerized from diol components/diisocyanate in methyl ethyl ketone or acetone under pressure at 80° C. for about 5 h, or from diamine/diisocyanate at a temperature of from 10 to 40° C. in ethanol.

Example

| | PEG1500 | A-Si2122 | PEG-DA | MDPTA | Hex-DA | IPDI |
|---|---|---|---|---|---|---|
| 1 | 3 | — | — | 1 | 1.2 | 5 |
| 2 | 3 | 0.5 | — | 1 | 0.7 | 5 |
| 3 | — | 0.5 | 3 | 1 | 0.7 | 5 |
| 4 | — | — | 3 | 1 | 1.2 | 5 |

PEG 1500: polyethylene glycol, Mn ≈ 1500 (BASF)
A-Si 2122: P(dimethylsiloxane-diamine), Mn ≈ 900 (Tegomer, Goldschmidt)
PEG-DA: 0,0'-bis(2-aminopropyl)polyethylene glycol 800; Mn ≈ 900 (Fluka)
MDPTA: N-methyldipropylenetriamine
Hex-DA: hexanediamine (1,6)
IPDI: isophorone diisocyanate

Examples 5–9

Cationic neutralizing polymer based on polyurethane (PUR) for COOH-containing polymers General preparation procedures:

For Example 7:

A four-necked flask, which had been fitted under an $N_2$ atmosphere with a stirrer, dropping funnel, thermometer and reflux condenser, was charged with 88.9 g (0.4 mol) of isophorone diisocyanate in 20 g of ethanol. At a temperature of about 10° C., a mixture of 90 g (0.1 mol) of Tegomer A-Si 2122 ($M_n$=900 g/mol) and 30 g of ethanol was added dropwise with stirring and ice cooling at a temperature of ≦40° C. The reaction was maintained at about from 30 to 40° C. under stirring for a further 30 minutes. After cooling to about 10° C., a mixture of 70 g (0.3 mol) of 0,0'-bis-(2-aminopropyl)polyether glycol 800; Mn≈900 (Fluka) and 2.9 g (0.02 mol) of N-methyuldipropylenetriamine in 50 g of ethanol was added, and the reaction temperature increased to about 45° C. The reaction mixture was then diluted with 600 g of ethanol. Filtration gave a clear pale yellow approximately 40% strength ethanolic polymer solution.

The neutralization polymers of Examples 5, 6, 8, 9 and also 12 and 13 were prepared in an analogous manner.

Example 10

Cationic neutralizing polymer based on polyacrylates (PA) for COOH-containing polymers General preparation procedures:

For Example 10:

| Feed 1: | vinylpyrrolidone | 59.5 g |
|---|---|---|
| | vinylcaprolactam | 102.0 g |
| | dimethylaminopropylmethacrylamide | 8.5 g |
| Feed 2: | ethanol | 80.0 g |
| | t-butylperpivalate | 0.4 g |
| Feed 3: | ethanol | 80.0 g |
| | t-butylperpivalate | 1.6 g |
| Initial charge: | ethanol | 95.0 g |
| | Feed 1 | 32.0 g |
| | Feed 2 | 10.0 g |

Method:

Heat the initial charge to 80° C. under $N_2$ in a stirring apparatus fitted with 3 feed units and with stirring. Then start Feed 1 and 2. Meter in Feed 1 in 3 h, and Feed 2 in 4 h. Afterpolymerize for 5 h at 80° C. Start Feed 3 and add at 80° C. in 1 h, and afterpolymerize for 5 h at 80° C. A colorless 40% strength ethanolic polyacrylate solution was obtained.

The neutralizing polymer 11 was prepared in an analogous manner.

| Ex. | Neutralizing polymer | VP | VCap | nBA | DMA PMA | AV |
|---|---|---|---|---|---|---|
| 10 | F | 35 | 60 | — | 5 | 16.5 |
| 11 | G | 55 | — | 40 | 5 | 16.5 |

VP: Vinylpyrrolidone
VCap: Vinylcaprolactam
DMAPMA. Dimethylaminopropylmethacrylamide
nBA: n-Butyl acrylate

| Ex. | Neutralizing polymer | PEG-DA (mol) | MDPTA (mol) | A-Si2122 (mol) | SO$_3$NA-PPG-DA (mol) | MAN 0078 (mol) | IPDI (mol) | AV |
|---|---|---|---|---|---|---|---|---|
| 5 | A | 3.5 | 1 | — | — | — | 4 | ca. 20 |
| 6 | B | 4.0 | — | 0.5 | — | — | 4 | 11.4 |
| 7 | C | 3.0 | 0.2 | 1 | — | — | 4 | 7.5 |
| 8 | D | 3.0 | — | 1 | 0.2 | — | 4 | 4.8 |
| 9 | E | 3.5 | 2–3 | — | — | 0.2 | 6 | 10 |

PEG-DA: O,O'-bis(2-aminopropyl)polyethylene glycol 800; Mn ≈ 900 (Fluka)
MDPTA: N-methyldipropylenetriamine
A-Si 2122: P(dimethylsiloxane-diamine), Mn ≈ 900 (Tegomer, Goldschmidt)
SO$_3$Na-PPG-DA: α, ω-polypropylene glycol diamine, sulfopropylated; Mn ≈ 700 (Raschig)
MA 00078: poly(aminopropyl)dimethylsiloxane (Hüls Silicone) amine value of about 28 (corresponds to diamine with molecular weight of ca. 4000)
AV: amine value
IPDI: isophorone diisocyanate

Example 12 and 13

Anionic neutralizing polymer based on polyurethane (PUR) for amino-containing polymers

| Ex. | Neutralizing polymer | PEG-DA | A-Si 2122 | DMPA | IPDI (mol) | AV |
|---|---|---|---|---|---|---|
| 12 | H | 3.0 | — | 1 | 4 | 15 |
| 13 | J | 2.5 | 0.5 | 1 | 4 | 15 |

A-Si 2122: P(Dimethylsiloxane-diamine), Mn ≈ 900 (Tegomer, Goldschmidt)
PEG-DA: 0,0'-bis(2-aminopropyl)polyethylene glycol 800; Mn ≈ 900 (Fluka)
AV: Acid value
DMPA: Dimethylolpropanoic acid
IPDI: Isophorone diisocyanate

Examples 14 to 16

Catonic neutralizing polymers

| Ex. | Neutralizing polymer | VP | nBA | TBA | DMAPMA | MAA | Belsil 6031 | AV |
|---|---|---|---|---|---|---|---|---|
| 14 | K | 70 | — | 21 | 6 | 3 | — | 19.9 |
| 15 | L | — | — | 5 | 5 | 5 | — | 16.5 |
| 16 | M | — | — | 70 | 3 | 22 | 5 | 9.9 |

TBA: t-Butyl acrylate
MAA: Methacrylic acid
Belsil 6031: Water-soluble ethoxylated silicone surfactant (Wacker Belsil DMC 6031)

Example 17

Preparation of COOH-containing polyurethane PUR® (base polymer I)

PUR of polyester-diol/neopentyl glycol/dimethylolpropanoic acid/isophorone diisocyanate 500 g [0.5 mol] of polyester-diol of isophthalic acid/adipic acid and 1,6-hexanediol (Mw=1000 g/mol), 201 g [1.5 mol] of dimethylolpropanoic acid (DMPA) and 104 g [1 mol] of neopentyl glycol (NPG) were dissolved in 370 g of methyl ethyl ketone with heating to a temperature of 80° C. and with stirring in a four-necked flask which was fitted with a stirrer, dropping funnel, thermometer, reflux condenser and equipment for operating under nitrogen. As soon as everything had dissolved, the reaction mixture was cooled to about 50° C. 699.3 g [3.15 mol] of isophorone diisocyanate were then added dropwise, and the reaction temperature increased. The reaction mixture was then stirred under reflux until the NCO content of the mNCO content of the mixture remained virtually constant. The mixture was then cooled to RT. The reaction product was shortstopped with 132.6 g [1.48 mol] of 2-amino-2-methyl-1-propanol (AMP)/water at a temperature of ≦40° C., and 90% neutralized. The solvent was then distilled off under reduced pressure at 40° C. to give an aqueous dispersion. Pulverulent polyurethanes can be obtained by spray drying.

Example 18

Preparation of COOH-containing polyurethane PUR® (base polymer II)

(PUR of polyester-diol/neopentyl glycol/dimethylolpropanoic acid/isophoronone diisocyanate/hexamethylene diisocyanate) 500 g [0.5 mol] of polyester-diol of isophthalic acid/adipic acid and 1,6-hexanediol (Mw=1000 g/mol), 201 g [1.5 mol] of dimethylolpropanoic acid (DMPA) and 104 g [1 mol] of neopentyl glycol (NPG) were dissolved in 370 g of methyl ethyl ketone with heating to a temperature of 80° C. an with stirring in a four-necked flask which was fitted with a stirrer, dropping funnel, thermometer, reflux condenser and equipment for operating under nitrogen. As soon as everything had dissolved, the reaction mixture was cooled to about 50° C. A mixture of 444 g [2 mol] of isophorone diisocyanate and 193.4 g [1.15 mol] of hexamethylene diisocyanate were then added dropwise, and the reaction temperature increased. The reaction mixture was then stirred under reflux until the NCO content of the mixture remained virtually constant. The mixture was then cooled to RT.

The reaction product was shortstopped with 132.6 g [1.48 mol] of 2-amino-2-methyl-1-propanol (AMP)/water at a temperature of ≦40° C., and 90% neutralized.

The solvent was then distilled off under reduced pressure at 40° C. to give an aqueous dispersion. Pulverulent polyurethanes can be obtained by spray drying.

Example 19

Preparation of polyacrylate of n-BA/TBA/MAA (40/35/25) (Base polymer III)

| Feed 1: | n-butyl acrylate (nBA) | 120.0 g |
|---|---|---|
|  | t-butyl acrylate (TBA) | 105.0 g |
|  | methacrylic acid (MAA) | 75.0 g |
| Feed 2: | ethanol | 100.0 g |
|  | t-butyl perpivalate | 0.9 g |
| Initial charge: | Feed 1 | 32.0 g |
|  | Feed 2 | 10.0 g |
| Feed 3: | ethanol | 150.0 g |
|  | t-butyl perpiv. | 1.6 g |
| Feed 4: | ethanol | 200.0 g |

Procedure: heat initial charge to 80° C. with stirring under $N_2$ in a stirring apparatus fitted with 4 feed units. Then start Feed 1 and 2, meter in Feed 1 over 3 h, and meter in Feed 2 over 4 h. Afterpolymerize for 2 h at 80° C. Start Feed 3 and add at 80° C. over 1 h, then afterpolymerize for 5 h at 80° C. Upon cooling, dilute with Feed 4.

Example 20

Preparation of COOH-containing polyacrylate PA® (from tert-butyl acrylate and methacrylic acid 75:25)

This product can be prepared by the general preparation procedure in Example 10.

Example 21

Preparation of amine-containing polyacrylate PA® (from tert-butyl acrylate, vinylpyrrolidone and DMAPMA (dimethylaminopropylmethacrylamide) (40:45:15))

This product can be prepared by the general preparation procedure in Example 10.

Example 22

Comparative Examples C1 to C5

| No. |  | Elasticity grade | Tensile strength | Feel | Tackiness | Wash-off | Clarity |
|---|---|---|---|---|---|---|---|
| C1 | Base polymer (I) PU neutralized with AMP | 3 | 2 | 2 | 1–2 | 1–2 | 1 |
| C2 | Base polymer (II) PU neutralized with AMP | 2 | 2–3 | 2–3 | 2–3 | 1 | 1 |
| C3 | Base polymer (III) PU neutralized with AMP | 2–3 | 2–3 | 2 | 2–3 | 1 | 1 |
| C4 | Neutralized polymer (C) | 2 | 3 | 1–2 | 3–4 | 2 | 1 |
| C5 | Neutralized polymer (G) | 2–3 | 2–3 | 2 | 3 | 1–2 | 1–2 |

Examples According to the Invention

| No. *) | Base polymer: neutralizing polymer [weight ratio] | Elasticity grade | Tensile strength | Feel | Tackiness | Wash-off | Clarity |
|---|---|---|---|---|---|---|---|
| 1 | (I):(A) = [9:1] | 2 | 1–2 | 2 | 1 | 1–2 | 1–2 |
| 2 | (I):(B) = [9:1] | 1–2 | 2 | 1 | 1 | 1–2 | 1 |
| 3 | (I):(C) = [9:1] | 1–2 | 2 | 1 | 1 | 1–2 | 1 |
| 4 | (I):(C) = [8:2] | 1 | 2 | 1 | 1–2 | 1 | 1 |
| 5 | (I):(C) = [7:3] | 1 | 2–3 | 1 | 2 | 1 | 1 |
| 6 | (I):(D) = [9:1] | 2 | 2 | 1–2 | 1 | 1 | 1 |
| 7 | (I):(E) = [9:1] | 1–2 | 1–2 | 1 | 1 | 1–2 | 1 |
| 8 | (II):(A) = [9:1] | 1–2 | 2 | 2 | 2 | 1 | 1–2 |
| 9 | (II):(B) = [9:1] | 1 | 2–3 | 1–2 | 1–2 | 1 | 1 |
| 10 | (II):(C) = [9:1] | 1 | 2 | 1–2 | 1–2 | 1 | 1 |
| 11 | (II):(D) = [9:1] | 1–2 | 2 | 1–2 | 1–2 | 1 | 1 |
| 12 | (II):(E) = [9:1] | 1 | 2 | 1 | 1–2 | 1 | 1 |
| 13 | (III):(A) = [9:1] | 2 | 2 | 2 | 2 | 1 | 1–2 |
| 14 | (III):(B) = [9:1] | 2 | 2–3 | 1–2 | 1–2 | 1 | 1 |
| 15 | (III):(C) = [9:1] | 2 | 2–3 | 1–2 | 1–2 | 1 | 1 |
| 16 | (III):(D) = [9:1] | 2 | 2–3 | 1–2 | 1–2 | 1 | 3–3 |
| 17 | (III):(E) = [9:1] | 2 | 2 | 1–2 | 1–2 | 1 | 1 |
| 18 | (I):(F) = [7:3] | 2–3 | 2 | 1–2 | 2 | 1 | 1 |
| 19 | (I):(G) = [7:3] | 2–3 | 2 | 2 | 1–2 | 1 | 1 |
| 20 | (II):(F) = [8:2] | 2 | 2–3 | 2 | 2 | 1 | 1 |
| 21 | (II):(G) = [8:2] | 2 | 2–3 | 2 | 1–2 | 1 | 1 |
| 22 | (II):(G) = [6:4] | 1–2 | 2–3 | 2 | 1–2 | 1 | 1 |
| 22a | (I):(K) = [5:5] | 3 | 2 | 1–2 | 1–2 | 1 | 1 |
| 22b | (II):(K) = [5:5] | 2 | 2 | 1–2 | 1–2 |  | 1 |
| 22c | (I):(K) = [4:6] | 2 | 2 | 1–2 | 1–2 | 1 | 1 |
| 22d | (II):(L) = [5:5] | 1–2 | 2 | 1–2 | 1–2 | 2–3 | 2 |
| 22e | (II):(M) = [7:3] | 1–2 | 2 | 1–2 | 1–2 | 1–2 | 1 |

*): All products were neutralized to a pH from 8 to 9 with neutralizing polymer and amino-2-methylpropanol.

Examples 23 to 25

Preparation of Polymeric salts

| | | Neutralized with Lactic acid (DN %) | Weight ratio*) | Weight ratio**) | Flexibility | Hold | Curl retention | Wash-off |
|---|---|---|---|---|---|---|---|---|
| C | PA$^\oplus$ | 100 | — | — | 3–4 | 1 | 78 | 1 |
| 23 | PA$^\oplus$ | 90 | 9:1 | — | 2–3 | 1 | 75 | 1 |

-continued

|  |  | Neutralized with | | Weight ratio*) | Weight ratio**) | Flexi-bility | Hold | Curl retention | Wash-off |
|---|---|---|---|---|---|---|---|---|---|
|  |  | Lactic acid (DN %) | | | | | | | |
| 24 | PA⊕ | 90 |  |  | 9:1 | 2–3 | 1 | 77 | 1 |
| 25 | PA⊕ | 90 |  |  | 8:2 | 2 | 1–2 | 74 | 1 |

C Comparative example: base polymer neutralized only with neutralizing agent lactic acid
PA⊕ Polyacrylate of tert-butyl acrylate, vinylpyrrolidone and dimethylaminopropylmethacrylamide 40:45:15 = base polymer as in Example 21
DN: Degree of neutralization
*) Base polymer: neutralizing polymer (H)
**) Base polymer: neutralizing polymer (J)

Example 26

Use as hair-setting polymer

|  | [%] |
|---|---|
| Aerosol hairspray | |
| Polymer No. 1-22 | 3.00 |
| Dimethyl ether | 40.00 |
| Ethanol | 57.00 |
| Other additives: silicone, perfume, antifoam . . . | |
| Aerosol hairspray | |
| Polymer No. 13-22 | 3.00 |
| Propane/butane gas | 40.00 |
| Ethanol | 57.00 |
| Other additives: silicone, perfume, antifoam . . . | |
| VOC 80 Aerosol hairspray | |
| Polymer No. 1-22 | 5.00 |
| Water | 15.00 |
| Dimethyl ether | 40.00 |
| Ethanol | 40.00 |
| Other additives: silicone, perfume, antifoam . . . | |
| VOC 55 Aerosol hairspray | |
| Polymer No. 1-12 and 16-22 and 22a-e | 3.00 |
| Water | 42.00 |
| Dimethyl ether | 35.00 |
| Ethanol | 20.00 |
| Other additives: silicone, perfume, antifoam . . . | |
| VOC 55 Hand pump spray | |
| Polymer No. 1-12 and 18-22 and 22a-e | 5.00 |
| Water | 40.00 |
| Ethanol | 55.00 |
| Other additives: silicone, perfume, antifoam . . . | |
| Setting foam (= mousse) | |
| Polymer No. 8-22 and 22a-e (25% strength aqueous solution) | 20.00 |
| Cremophor A 25 (Ceteareth 25/BASF) | 0.20 |
| Comperlan KD (Cocamide DEA/Henkel) | 0.10 |
| Water | 69.70 |
| Propane/butane | 10.00 |
| Other additives: perfume, preservatives . . . | |

Preparation: Weigh in and dissolve with stirring. Bottle and add propellant.

|  | [%] |
|---|---|
| Conditioning shampoo | |
| A) Texapon NSO 28% strength (Sodium Laureth Sulphate/Henkel | 50.00 |
| Comperlan KD (Cocamide DEA/Henkel) | 1.00 |
| Polymer 22, 22a-e (25% strength aqueous solution) | 20.00 |
| q.s. Perfume oil | |
| B) Water | 27.50 |
| Sodium chloride | 1.50 |
| q.s. preservatives . . . | |

Preparation: Weigh in and dissolve separately phases A and B with stirring and mix. Slowly stir phase B into phase A.

Standard O/W cream

|  | [%] |
|---|---|
| Oil phase | |
| Paraffin oil | 7.50 |
| Ceteareth-6 and stearyl alcohol | 3.50 |
| Ceteareth-25 | 3.50 |
| Cetyl alcohol | 3.50 |
| Glyceryl monostearate s.e. | 2.50 |
| Cetearyl octanoate | 3.20 |
| Methyl- and propyl-4-hydroxybenzoate | (7:3) |
| Tocopheryl acetate | 1.00 |
| Water phase | |
| Polymer 1-22 and 22a-e | 1.50 |
| Water | 74.60 |
| Imidazolidinylurea | 0.10 |

Preparation: Weigh in and homogenize with stirring the oil phase and water phase separately at a temperature of about 80° C. Slowly stir the water phase into the oil phase. Slowly cool to RT with stirring.

We claim:

1. A water-soluble or water-dispersible polymeric salt comprising
   A) a base polymer which contains an ionic or ionogenic group, and
   B) a neutralizing polymer, which are film-forming and water-dispersible which partially neutralizes the ionic or ionogenic group of the base polymer A, where the ionogenic groups of the base polymer A are more frequent by a factor of from 2 to 30 than the ionogenic groups of the neutralizing polymer B wherein at least one of the base polymer A and the neutralizing polymer B is a polyurea.

2. A film-forming auxiliary comprising a polymeric salt as claimed in claim 1.

3. A polyurethane, poly(urethane-urea) or polyurea as base polymer as claimed in at least one of claim 1, constructed from:
  f) at least one compound which contains two (or more) hydrogen atoms per molecule, having a number average molecular weight in the range from about 300 to 5000.

4. A polyacrylate as base polymer A as claimed in claim 1, constructed from:
  at least one $C_1$–$C_4$-alkylacrylic ester or $C_1$–$C_4$-alkylmethacrylic ester or acrylamide or methacrylamide or $C_1$–$C_4$-alkylacrylamide and or $C_1$–$C_4$-alkylmethacrylamide,
  at least one COOH-containing monomer.

5. A neutralizing polymer B as claimed in claim 1, which is a film-forming polymer which is dispersible with water.

6. A polyurethane, poly(urethane-urea) or polyurea as neutralizing polymer B as claim 5, constructed from:
  j) at least one compound or a mixture of compounds carrying at least two active hydrogen atoms per molecule and having a molecular weight of from 56 to 6000 g/mol, where at least one compound contains one of the following groups:
    —(—$CH_2$—$CH_2$O—)m—($C_3H_6$O—)n—, where the order of the alkylene oxide units is arbitrary, and m and n independently of one another are an integer from 0 to 50, and the sum m+n is in the range of from 5 to 60,
    —COO—, —$SO_3^-$ or
    —$N^+$ group-(quaternized amines),
  k) optionally a compound having at least two active hydrogen atoms per molecule and at least one ionogenic group,
  l) at least one amino-containing poly(dimethylsiloxane) and
  m) at least one diisocyanate,
  where the acid value or amine value is not greater than 60.

7. A neutralizing polymer as claimed in claim 6, where the components are present in the following amounts:
  j) 10 to 90% by weight
  k) 0 to 20% by weight
  l) 0.1 to 30% by weight
  m) 5 to 30% by weight, based on j+k+l+m.

8. A neutralizing polymer B as claimed in claim 1, constructed from at least one vinyllactam and/or at least one vinylamide and at least one amine-containing monomer, where the amine value is between 1 and 60.

9. A neutralizing polymer B as claimed in claim 1, constructed from at least one $C_1$–$C_{18}$-alkylmethacrylic ester and/or $C_1$–$C_{18}$-alkylmethacrylamide and at least one amine-containing and/or COOH-containing monomer.

10. A process for the preparation of polymeric salts as in claim 1, where the base polymer A is partially neutralized in a suitable solvent with a monovalent neutralizing agent, and then the neutralizing polymer B is added.

11. A setting polymer in hair cosmetics, hair sprays, hair foams and shampoos comprising a polymeric salt as claimed in claim 1, wherein said polymeric salt has a glass transition temperature of >10° C.

12. An additive for cosmetic preparations comprising a polymeric salt as claimed in claim 1.

13. A conditioning polymer in hair cosmetics, hair sprays, hair foams and shampoos comprising a polymeric salt as claimed in claim 1, wherein said polymeric salt has a glass transition temperature of >10° C.

* * * * *

UNITED STATES PATENT AND TRADEMARK OFFICE
CERTIFICATE OF CORRECTION

PATENT NO.    : 6,410,004 B1
DATED         : June 25, 2002
INVENTOR(S)   : Kim et al.

It is certified that error appears in the above-identified patent and that said Letters Patent is hereby corrected as shown below:

<u>Column 27,</u>
Line 9, delete "at least one of".
Line 15, "5000." should be:
-- 5000,
g)   at least one compound which contains two active hydrogen atoms per molecule and has a molecular weight of from 56 to 300 g/mol,
h)   at least one phosphate-, phosphonate-, COO$^-$, SO$_3^-$, and/or tert-amine-containing compound or compounds thereof which contain the free acids that contain two active hydrogen atoms per molecular, and
i)   at least one diisocyanate. --
Line 20, "and or" should be -- or --.
Line 21, after "alkylmethacrylamide," insert -- and --.
Line 27, after "as" insert -- in --.

Signed and Sealed this

Twelfth Day of November, 2002

*Attest:*

JAMES E. ROGAN
*Attesting Officer*   *Director of the United States Patent and Trademark Office*